United States Patent [19]

Cleveland

[11] Patent Number: 4,947,690
[45] Date of Patent: Aug. 14, 1990

[54] ACCELETOMETERS ADAPTED FOR EFFICIENT CONNECTION AND DISCONNECTION

[75] Inventor: Lester G. Cleveland, San Juan Capistrano, Calif.

[73] Assignee: Allied-Signal Inc., Morris Township, N.J.

[21] Appl. No.: 374,403

[22] Filed: Jun. 29, 1989

[51] Int. Cl.⁵ ..................... G01H 11/06; G01P 15/08
[52] U.S. Cl. ........................................ 73/654; 73/493
[58] Field of Search ..................... 73/493, 517 R, 654, 73/866.5; 310/329

[56] References Cited

U.S. PATENT DOCUMENTS

| | | | |
|---|---|---|---|
| 4,347,743 | 9/1982 | Rausche et al. | 73/654 |
| 4,771,637 | 9/1988 | Kubler | 73/493 |
| 4,858,470 | 8/1989 | Kincaid et al. | 73/654 |

Primary Examiner—John Chapman
Attorney, Agent, or Firm—Robert C. Smith; Joseph R. Black; James W. McFarland

[57] ABSTRACT

The invention provides an accelerometer (10) which can be connected to or disconnected from a support structure (12) by means of a single fastening component (18) while holding remaining structural components (14, 16, 20) at a fixed azimuthal position relative to the top surface (38) of the support structure (12).

9 Claims, 2 Drawing Sheets

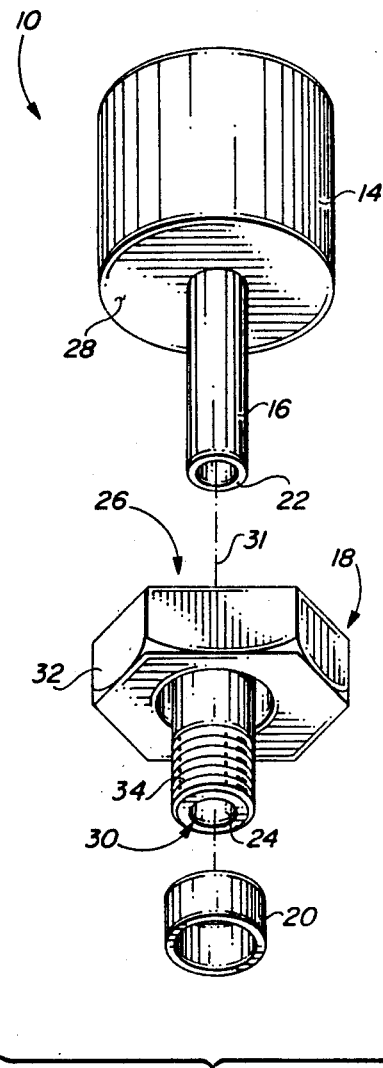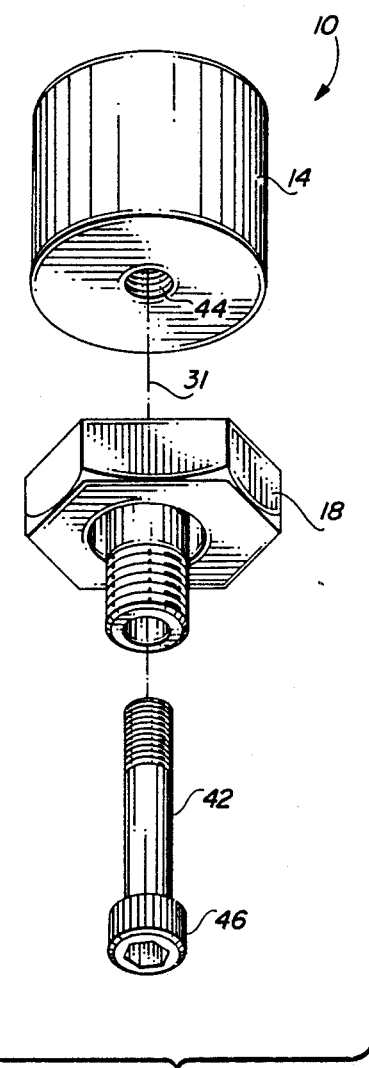

ACCELETOMETERS ADAPTED FOR EFFICIENT CONNECTION AND DISCONNECTION

TECHNICAL FIELD

The present invention relates generally to accelerometers. More particularly, the invention provides accelerometers with fastening components which facilitate installation and replacement.

BACKGROUND OF THE INVENTION

Accelerometers (devices used for measuring acceleration or for detecting and measuring vibration) can be mounted to support structures by a variety of known methods. These methods can be more or less cumbersome depending on such application-driven factors as design specification and space limitation.

For example, a customer may demand accelerometers with cables which are rigidly secured to the accelerometer and not designed for removal therefrom. Often, it is desirable to mount such accelerometers to the support structure with a single connector by employing a centerbolted design or a threaded stud. Securement then requires that the accelerometer be rotated along with the protruding cable as the bolt or stud is driven into a tapped bore which is formed in the support structure. This task is inherently cumbersome, and is made more so in applications which provide very limited working space.

Other problems arise when the accelerometer must be secured to the support structure and then connected to an already-positioned cable. Unless the tapped bore in the support structure is very precisely dimensioned in relation to the accelerometer (which, ordinarily, is not the case), the cable connector of the accelerometer will probably not be aligned with the cable when the accelerometer is secured to the structure. If the cable isn't sufficiently long and flexible, or if space limitations preclude the use of longer cables, spacers may be used between the accelerometer and the support structure in a trial-and-error process until the required alignment is provided. However, the use of spacers will adversely affect the frequency response and robustness of the accelerometer.

SUMMARY OF THE INVENTION

This invention solves the forementioned problems by providing an accelerometer that can be connected to a support structure with a single fastening component while holding the remainder of the accelerometer in a substantially fixed azimuthal position relative to the top surface of the support structure. The fastening component is a bolt-like member of the accelerometer that is free to rotate about a shaft which extends through the member in an axial direction. The member, however, is constrained from moving in either axial direction thereof.

DESCRIPTION OF THE PREFERRED EMBODIMENT

Figure 2:
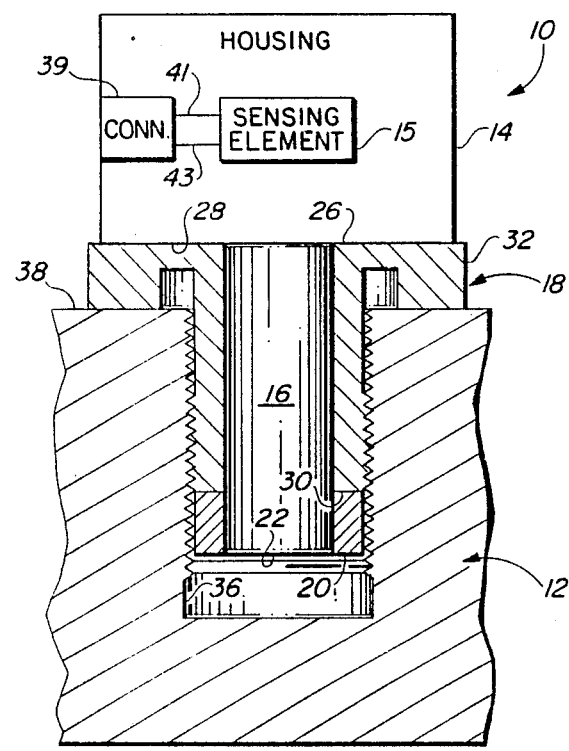

FIG. 1 illustrates an accelerometer 10 adapted for securement to a support structure 12 (FIG. 2) in accordance with a specific embodiment of the invention. The support structure 12 may be the hull of a submarine, for example. However, the support structure 12 may be any structure that serves as a mounting base for the accelerometer 10 in a given application. The accelerometer 10 comprises a housing structure 14 which contains a sensing element 15 (FIG. 2 - typically, this is a piezoelectric or piezoresistive element), a cylindrical shaft 16 that is formed integrally with the housing structure, a bolt-like member 18, and an annulet 20. The shaft 16 extends from the housing structure 14 to its distal end 22, and is received in an axiallyextending hole 24 formed in the member 18. The shaft 16 is extended through the member 18 until a first end 26 of the latter abuts the bottom surface 28 of the housing structure 14. The shaft 16 is sufficiently long relative to the member 18 to ensure that a distal portion of the former projects beyond a second end 30 of the latter. The annulet 20 is pressed onto the shaft 16 until it abuts the second end 30 of the member 18, and is fusion welded to the shaft. The hole 24 and shaft 16 are dimensioned such that the member 18 can be easily rotated around the shaft. There is thus provided an essentially zero-clearance fit between the first end 26 and the bottom surface 28, and between the second end 30 and the annulet 20. This fit renders the member 18 substantially immovable relative to the shaft 16 and housing structure 14 in axial directions (indicated by the dashed line 31) dashed line 31) of the member. However, the fit must not be so tight as to prevent manual rotation of the member 18 around the shaft 16.

The member 18 is adapted for engagement with a torquing tool via a head 32, and is adapted for engagement with the support structure 12 (FIG. 2) via a threaded outer surface 34.

Referring to FIG. 2 wherein the accelerometer 10 is shown assembled and extended into a tapped bore 36 formed in the support structure 12, it can be seen that if the head 32 is torqued, the member 18 will push downwardly against the annulet 20. Since the annulet 20 is rigidly secured to the shaft 16 and the latter is rigidly secured to the housing structure 14, the downward force is transferred to the housing structure and the entire accelerometer 10 is carried with the member 18. This causes the bottom surface 28 to press hard against the first end 26 of the member 18, effecting a friction lock between the member 18 and the top surface 38 of the support structure 12, and between the bottom surface 28 of the housing structure 14 and the first end 26 of the member.

Figure 3:
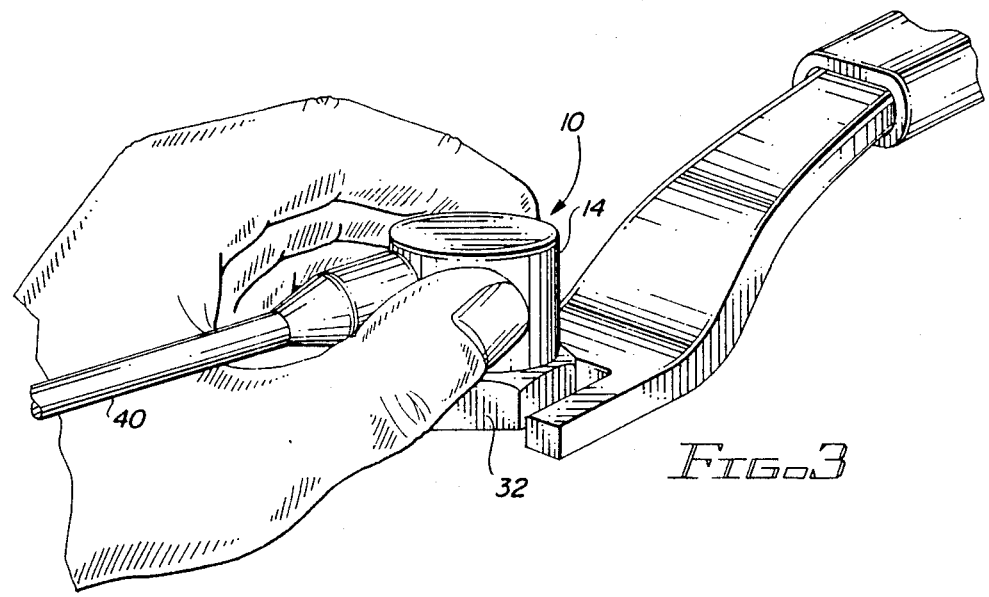

FIG. 3 illustrates the primary benefit provided by the invention. As previously stated, the housing structure 14 contains a sensing element 15. Accordingly, the housing is adapted, by any conventional means (a connector 39 and two leads 41, 43 are shown schematically) to provide for electrical communication between the internal sensing element 15 and a remote signal processing system (not shown). Irrespective of the particular means employed to that end, a cable, shielded wire-pair, or other conventional electrical communication channel 40 must be secured to the housing structure 14. The azimuthal position of the housing structure 14 relative to the top surface 38 of the support structure 12 may be held substantially fixed as illustrated, while the accelerometer 10 is connected to or disconnected from the support structure 12 by torquing the head 32 in the appropriate direction. Therefore, regardless of whether the communication channel 40 is secured to the accelerometer 10 before or after installation, the above-described problems are eliminated.

FIG. 4 illustrates another among many possible embodiments of the invention. The shaft 16 (FIG. 1) is provided in the form of a cap screw 42 which is extended through the member 18 and rigidly secured to the housing structure 14 by engagement with a tapped bore 44. An epoxy is applied to the threads of the bore 44 prior to engagement. The boss or head 46 of the cap screw 42 provides the function of the annulet 20 (FIG. 1).

Despite the illustrated embodiments, it is unnecessary that the shaft 16 be cylindrical along its entire length so long as a cylindrical portion is provided for the purpose of rotating the member around that portion.

Other embodiments of the invention could include the following exemplary elements which provide the functions performed in the embodiment of FIG. 1 by the annulet 20 or the bottom surface 28: 1) a boss on the shaft 16 performing the function of the bottom surface 28; 2) a washer or other spacer-type element interposed between the housing structure 14 and the member 18 and performing the function of the bottom surface 28; 3) a pin extending through a hole drilled transversely trough the shaft 16 near the distal end 22, the pin performing the function of the annulet 20; and 4) one or more bosses on the housing structure 14 performing the function of the bottom surface 28.

The foregoing text and accompanying drawings are not intended to restrict the scope of the invention to specific details which are ancillary to the teaching contained herein. Accordingly, the invention should be construed in the broadest manner which is consistent with the following claims and their equivalents.

What is claimed is:

1. An accelerometer adapted for facile securement to a support structure, comprising:
   a housing structure that contains a sensing element;
   a shaft rigidly secured to or integral with said housing structure; said shaft extending to a distal end thereof in a direction away from said housing structure; said shaft having a cylindrical portion between said housing structure and said distal end;
   a bolt-like member coaxial with said cylindrical portion and having a hole which extends in said direction from a first end to a second end of said member; said cylindrical portion extending through said hole and said member being easily rotatable about said portion; said member being adapted for engagement with a torquing tool and having an outer surface which is adapted for engagement with said support structure: and
   means for retaining said member in a substantially fixed axial position relative to said cylindrical portion whereby if said member is displaced in either axial direction, said shaft and said housing structure are carried therewith.

2. The invention of claim 1 wherein said shaft extends beyond said second end of said member, and wherein said retaining means comprises an annulet rigidly secured to said shaft and abutting said second end.

3. The invention of claim 2 wherein said retaining means cooperates with said housing structure to prevent axial displacement of said member relative to said cylindrical portion, said first end abutting said housing structure.

4. The invention of claim 1 wherein said retaining means is provided at least in part by an annular boss of said shaft.

5. The invention of claim 1 wherein said retaining means comprises a boss on said shaft and cooperates with said housing structure to render said member substantially immovable relative to said cylindrical portion in said axial directions.

6. An accelerometer adapted for securement to a support structure by a single fastening component, whereby all components of said accelerometer except said fastening component can be held at a substantially fixed azimuthal position relative to a top surface of said structure during said securement, comprising:
   a housing structure that contains a sensing element;
   a shaft rigidly secured to or integral with said housing structure; said shaft extending to a distal end thereof in a direction away from said housing structure; said shaft having a cylindrical portion between said housing structure and said distal end;
   a bolt-like member coaxial with said cylindrical portion and having a hole which extends in said direction from a first end to a second end of said member; said cylindrical portion being disposed in said hole and said member being easily rotatable about said portion; said member being adapted for engagement with a torquing tool and having an outer surface which is adapted for engagement with said support structure; and
   means abutting said second end for retaining said member to limit displacement thereof in said direction,
   said member being substantially immovable relative to said cylindrical portion in axial directions, whereby if said member is displaced in either axial direction, said shaft and said housing structure are carried therewith.

7. The invention of claim 6, wherein said retaining means cooperates with said housing structure to render said member substantially immovable in said axial directions.

8. The invention of claim 6 wherein said retaining means comprises a boss on said shaft.

9. An accelerometer adapted for facile securement to a support structure, comprising:
   a housing structure that contains a piezo-type sensing element;
   a bolt-like member having an axially-extending hole formed therethrough; said hole extending from a first end of said member which faces said housing structure to an oppositely-facing second end of said member; said member being adapted for engagement with a torquing tool and having an outer surface which is adapted for engagement with said support structure; and
   a cylindrical shaft rigidly secured to or integral with said housing structure and around which said member is rotatable; said shaft being coaxial with said member and extending between said first and second ends;
   said member being secured so as to be substantially immovable in axial directions thereof relative to said housing structure and to said shaft.

* * * * *